United States Patent [19]

Nielsen

[11] Patent Number: 4,608,041
[45] Date of Patent: Aug. 26, 1986

[54] DEVICE FOR TREATMENT OF WOUNDS IN BODY TISSUE OF PATIENTS BY EXPOSURE TO JETS OF GAS

[76] Inventor: Frese Nielsen, Rosenlundsvägen 42, S-440 80 Ellös, Sweden

[21] Appl. No.: 504,689
[22] PCT Filed: Oct. 11, 1982
[86] PCT No.: PCT/SE82/00325
 § 371 Date: Jun. 13, 1983
 § 102(e) Date: Jun. 13, 1983
[87] PCT Pub. No.: WO83/01388
 PCT Pub. Date: Apr. 28, 1983

[30] Foreign Application Priority Data

Oct. 14, 1981 [SE] Sweden .......................... 8106069

[51] Int. Cl.$^4$ .................................................. A61F 2/36
[52] U.S. Cl. .................................... 604/23; 128/118; 128/155; 604/289; 604/305
[58] Field of Search ............... 128/114, 118, 24.1, 128/155, 156; 604/23, 305, 289

[56] References Cited

U.S. PATENT DOCUMENTS

| | | |
|---|---|---|
| 2,998,817 | 9/1961 | Armstrong .......................... 604/23 |
| 3,089,492 | 5/1963 | Owens .................................. 604/305 |
| 3,467,081 | 9/1969 | Glass .................................... 128/24.2 |
| 3,610,238 | 4/1970 | Rich, Jr. ............................... 604/23 |
| 3,920,006 | 11/1975 | Lapidus ................................ 604/23 |
| 4,182,329 | 1/1980 | Smit et al. ............................ 604/23 |
| 4,224,941 | 9/1980 | Stivala .................................. 604/23 |

FOREIGN PATENT DOCUMENTS 0789692 11/1935 France ................................. 604/23

Primary Examiner—C. Fred Rosenbaum
Assistant Examiner—Gene B. Kartchner

[57] ABSTRACT

Device for treatment of wounds in body tissue of patients by means of jets of gas. A nozzle unit is designed to be placed over the area of the wound in order to cover it and is provided with inlets (6,10) for admission of oxygen gas to the area of the wound and outlets (9) for discharge of oxygen gas from the area of the wound. The inlets are designed to be connected by a hose (7) to a source of pressure containing air or oxygen gas. The nozzle unit is made of at least two layers of plastic foil (1,2) which are joined along the major part of their edges (3) enclosing an inner space, maintained mainly by the gas pressure, into which space the inlet (6) directs the flow. The nozzle unit is provided with a plurality of inlet openings (10) giving admission from the inner space (11) which openings are disposed in the layer of plastic foil (2) which is nearest to the area of the wound when the device is in use. These are designed to direct a plurality of gas jets at the area of the wound. A plurality of outlet openings (9) are so disposed in both layers of plastic foil (1,2) that gas from the area of the wound is made to escape out of the nozzle unit without passing through the inner space (11) on its way from the area of the wound.

5 Claims, 2 Drawing Figures

DEVICE FOR TREATMENT OF WOUNDS IN BODY TISSUE OF PATIENTS BY EXPOSURE TO JETS OF GAS

TECHNICAL FIELD

The invention relates to a device for treatment of wounds in body tissue of patients by exposure of the area of the wound to jets of gas. The device consists of a nozzle pressure unit designed to be placed over the area of the wound in order to cover it, and is provided with an inlet allowing pressure gas to reach the area of the wound and an outlet allowing gas to leave the area of the wound, the inlet of the nozzle pressure unit consisting of a main inlet opening leading to an enclosed space separated from the area of the wound and into which space the gas is passed, and in addition consisting of a plurality of inlet openings leading from the above-mentioned space to the area of the wound.

BACKGROUND

Treating a wound with gas, for example oxygen gas, in order to hasten healing of the wound and reduce itching is known, and as a rule it is done by applying a jet of oxygen gas to the wound. Usually this is carried out by means of the end of a hose being held so as to aim at the wound, which requires the presence of staff who have to hold the hose and keep an eye on the exposed wound.

The technical problem

The object of the present invention is to provide a device by means of which continuous treatment with oxygen gas can be carried out without the necessity of staff being present all the time.

The solution

Said object is achieved by means of a device which is characterized in that the nozzle unit is provided with a plurality of outlet openings forming said outlet, which openings are designed to let out the gas straight from the area of the wound into the environment without the gas passing through the abovementioned space on its way from the area of the wound, and in that the inlet openings and the outlet openings are distributed together over the surface of the nozzle unit facing the area of the wound in such a manner that the inlet openings direct a plurality of gas jets at the area of the wound and the outlet openings discharge gas from several different places between the inlet openings.

BRIEF DESCRIPTION OF DRAWINGS

A more detailed description of the invention is given below by means of an example of embodiment with reference to attached drawings in which.

BEST MODE OF CARRYING OUT THE INVENTION

Figure 2:
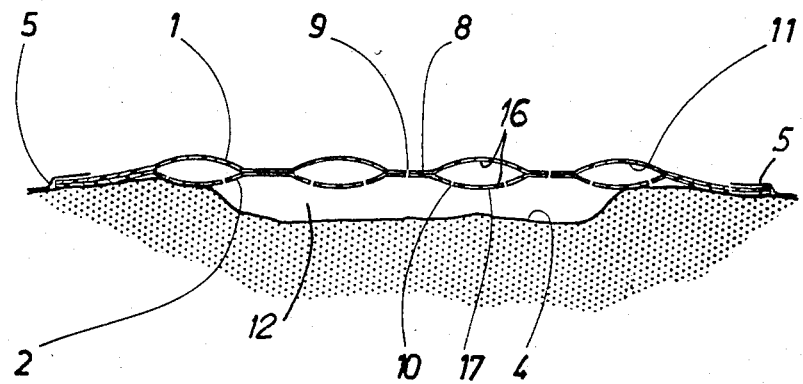
FIG. 2 shows a diagrammatic cross section of the device according to the invention applied over a wound of a patient.

The device according to the invention is embodied as a nozzle unit consisting of two layers of plastic foil 1, 2 which are welded or stuck together along an area of their outer edges 3 which is utilised for fixing the unit over the area of a wound 4 (see FIG. 2). The fixing can be carried out by means of plaster, tape 5, or the like. The unit is provided with an inlet opening 6 and an inlet hose 7 connected to a source of pressure gas containing oxygen gas, air, or the like. The device is provided with several sections 8, in the example shown three, along which the two layers of plastic foil 1, 2 are joined by means of welding, glueing or the like. In these sections the device is provided with a plurality of through-going outlet openings 9, disposed in rows which openings thus go through both layers of plastic foil 1, 2. Next to these rows of outlet openings 9, comprising in the example shown three rows of thirteen openings each, there are a number of rows of inlet openings 10. To be more explicit, double rows of inlet openings 10 are situated between the rows of outlet openings 9, while outside the rows of outlet openings 9 extend a row of inlet openings 10 rectangularly. The inlet openings 10 are disposed in only one of the layers of plastic foil, namely the one shown in FIG. 2 and marked 2, these openings thus being directed towards the area of the wound 4. The inlet openings 10 as well as the outlet openings 9 are made simply by perforating the layers of plastic foil.

When the interior of the device is connected to the gas supply by way of the inlet hose 7 there is formed a space 11, constituting a connected whole and having cushion-like parts which are inflated by the gas pressure, and thus are produced a great number of jets of gas passing first through the inlet openings 10 which direct the jets at the area of the wound 4. The unit being fixed over the area of the wound, there is formed an air-filled space 12 above the area of the wound from which the oxygen gas can escape through the outlet openings 9 into the air outside. In the cushion-like parts domed surfaces 16 are formed in the layers of plastic foil 1, 2. The rows of inlet openings 10 being oriented next to an imaginary center line between the parallel sections 8, the inlet openings and consequently the jets of gas are made oblique in relation to the area of the wound 4, and the jets are thrown back towards the adjacent rows of outlet openings 9. Hereby is obtained a very effective and even treatment of the area of the wound, obviating the necessity of supervising staff. This is particularly advantageous as the treatment in question is frequently carried on for a long period of time, which would otherwise be costly. The effect of the treatment by means of the device according to the invention is very even, the area of the wound being shielded from the outside air whereby is achieved a particularly good healing effect because of the high concentration of sterile air or oxygen gas in the area of the wound in the absence of room air which always contains a certain amount of germs. The nozzle unit gives gentle protection to the area of the wound, especially when the latter is subjected to contact pressure, for example when the patient is lying down, the unit forming a pressure relieving, protective cushion which, activated by the gas pressure in the area of the wound, endeavours (sic) to avoid touching the surface of the wound.

Figure 1:
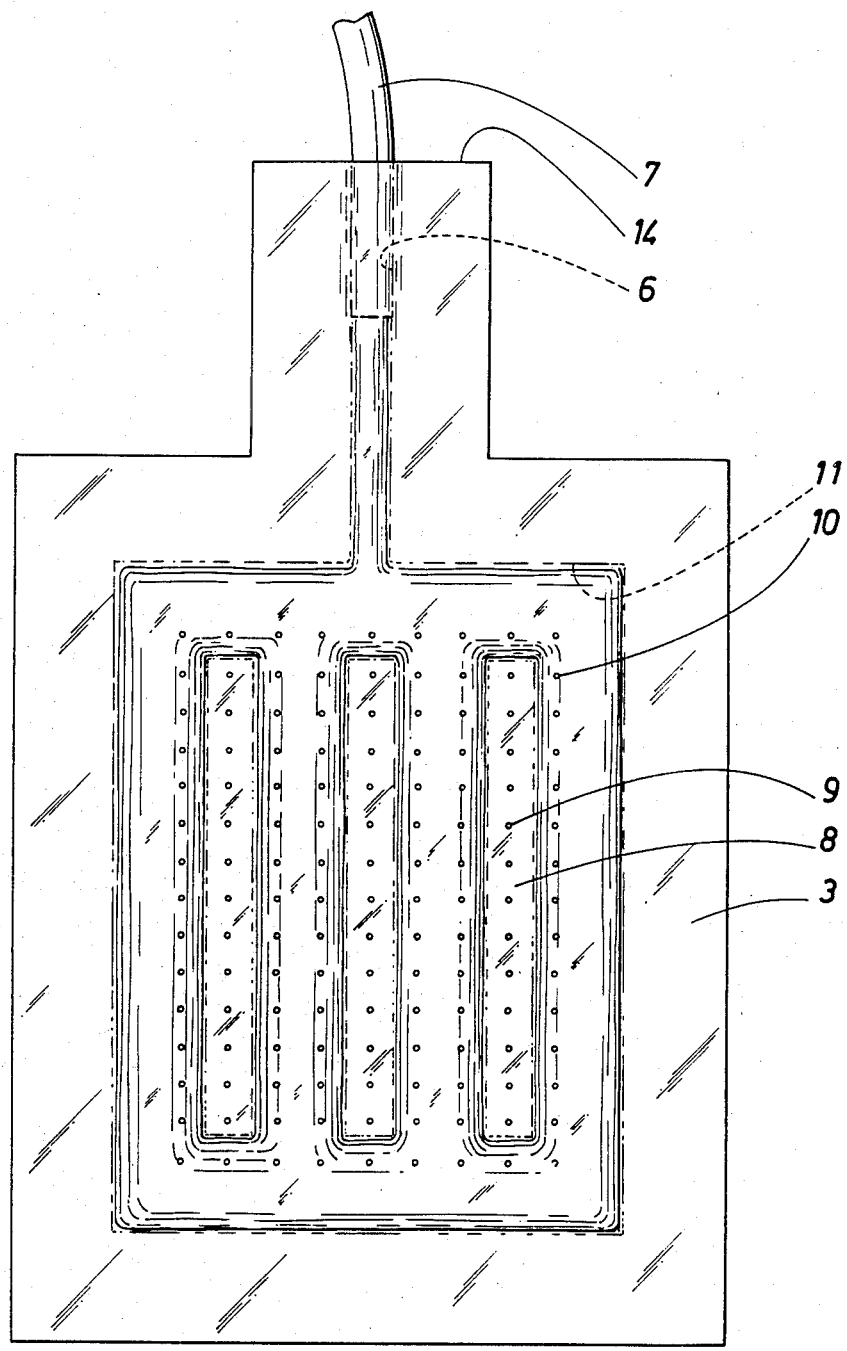
FIG. 1 shows a view from above of the device according to the invention.

The nozzle unit according to the invention can be made very simply and cheaply and should subsequently be sterilised and packed in sterile wrapping. The device is particularly space-saving, as it is very flat when packed and, with the exception of the hose connection 7, is of a total thickness of two layers of plastic foil. The unit might possibly be supplied without the hose and only provided with the passage 6 shown in FIG. 1 and formed where the two layers of plastic foil 1, 2 are not welded together, an area extending from the part of the edge 14 of the layers of plastic foil to the inner space 11. With the device can be used an inlet hose 7 otherwise belonging to the oxygen gas equipment and designed to be simply pushed into the inlet passage 6 of the nozzle unit for connection to it. The inlet hose 7 should in this case preferably have a conical or pointed end to facilitate its insertion.

The invention is not limited to the above described example of embodiment shown in the drawings, but can be varied within the scope of the following claims. The rows of inlet and outlet openings can, for example, be arranged differently.

I claim:

1. A device for treating a wound in body tissue of a patient, comprising: a nozzle unit to be placed over the wound so as to cover the wound and to separate the wound from surrounding space, an inlet for gas under pressure to the unit, said unit including a first and second layer of plastic foil, both having first surfaces where the layers are sealingly joined to each other including surfaces extending along a major part of the circumference of the unit, said first and second layers defining an inner space, said inlet communicating with said inner space so as to be sustained at least partly by gas pressure separating the first and second layers from each other at second surfaces, said first layer having a plurality of inlet openings leading from said inner space to the wound, said inlet openings being positioned in said second surfaces of said first layer, there being two rows of inlet openings with each row being displaced relative to a centerline between the two rows so that when the nozzle unit adjacent to each inlet opening assumes a curved configuration each inlet opening will be slanted with respect to the wound and a jet of gas exiting from each inlet opening will be directed obliquely at the wound, said first and second layers having a plurality of outlet openings positioned in at least part of said first surfaces, said outlet openings leading from the area of the wound directly to the surrounding space, so that the inlet openings may direct a plurality of gas jets from the inner space to the wound, and the outlet openings may let out gas directly to the surrounding space from the wound.

2. A device according to claim 1, wherein the inlet openings are disposed in a number of first spaced rows, and the outlet openings are disposed in a number of second rows alongside the first rows.

3. A device according to claim 2, wherein the rows of outlet openings are disposed in oblong sections, one section for each row, in said first surfaces of the two layers.

4. A device according to claim 1, wherein the inlet openings and the outlet openings are so dimensioned that excess pressure is created in a space between the nozzle unit and the wound.

5. A device according to claim 4, wherein said sections extend parallel to each other and have ends finishing at some distance from the circumference of the nozzle unit in such a manner that said inner space becomes a connected whole and when under gas pressure, forms cushion-like parts with domed surfaces.

* * * * *